US007135321B2

(12) United States Patent
Harrison et al.

(10) Patent No.: US 7,135,321 B2
(45) Date of Patent: Nov. 14, 2006

(54) GSK3 POLYPEPTIDES

(75) Inventors: Stephen D Harrison, Albany, CA (US); John A Hall, Rohnert Park, CA (US); Maria Calderon-Cacia, Castro Valley, CA (US); Ziyang Zhong, Union City, CA (US); Eric Y Fang, Oakland, CA (US); Doris G Coit, Petaluma, CA (US); Steve H Nguyen, San Francisco, CA (US); Angelica Medina-Selby, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 443 days.

(21) Appl. No.: 10/689,461

(22) Filed: Oct. 20, 2003

(65) Prior Publication Data

US 2005/0048511 A1    Mar. 3, 2005

Related U.S. Application Data

(62) Division of application No. 10/211,412, filed on Jul. 31, 2002, now Pat. No. 6,716,624, which is a division of application No. 09/916,109, filed on Jul. 25, 2001, now Pat. No. 6,465,231.

(60) Provisional application No. 60/221,242, filed on Jul. 27, 2000.

(51) Int. Cl.
*C12N 9/12* (2006.01)
*C12Q 1/48* (2006.01)
*C12P 21/06* (2006.01)
*C12N 15/54* (2006.01)
*C12N 15/70* (2006.01)
*C12N 5/00* (2006.01)
*C12N 1/00* (2006.01)
*C07H 21/04* (2006.01)

(52) U.S. Cl. ............ 435/194; 435/15; 435/320.1; 435/69.1; 435/252.3; 435/325; 536/23.1; 536/23.2; 536/23.5; 530/350

(58) Field of Classification Search ............ 435/194, 435/15, 320.1, 69.1, 252.3, 325; 536/23.1, 536/23.2, 23.5; 530/350

See application file for complete search history.

(56) References Cited

U.S. PATENT DOCUMENTS 6,057,117 A     5/2000   Harrison et al.

FOREIGN PATENT DOCUMENTS

WO     WO-99/65897     12/1999

OTHER PUBLICATIONS

Bax et al., Structure 9:1143-1152, 2001.*

Summers et al., *The Role of Glycogen Synthase Kinase 3β in Insulin-Stimulated Glucose Metabolism*, Journal of Biological Chemistry, 274(25):17934-17940, 1999.
GenBank accession No. AAA 84444 1996.
Database EMBL Entry, Accession No. P49840, 1996.
Database EMBL Entry, Accession No. P49841, 1996.
Database EMBL Entry, Accession No. Q91627, 1996.
Database EMBL Entry, Accession No. U31862, 1995.
Latimer et al., *Stimulation of MAP Kinase by V-Raf Transformation of Fibroblasts Fails to Induce Hyperphosporylation of Transfected Tau*, FEBS Letters, 365(1):42-46, 1995.
Cross et al., *The Inhibition of Glycogen Synthase Kinase-3 by Insulin-Like Growth Factor 1 in the Rat Skeletal Muscle Cell Line L6 is Blocked by Wortmannin, but Not by Rapamycin: Evidence that Wortmannin Blocks Activation of the Mitogen-Activiated Protein Kinase Pathway in L6 Cells Between Ras and Raf*, Biochemical Journal, 303(Part 1):21-26, 1994.
Lovestone et al., *Alzheimer's Disease-Like Physphorylation of the Microtubule-Associated Protein Tau by Glycogen Synthase Kinase-3 in Transfected Mammalian Cells*, Current Biology, 4(12):1077-1086, 1994.
Mulot et al., *PHF-Tau from Alzheimer's Brain Comprises Four Species on SDS-PAGE Which Can Be Mimicked by in Vitro Phosphorylation of Human Brain Tau by Glycogen Synthase Kinase-3β*, FEBS Letters, 349(3):359-364, 1994.
Peifer et al., *Phosphorylation of the Drosophilia Adherens Junction Protein Armadillo: Roles for Wingless Signals and Zeste-White 3 Kinase*, Developmental Biology, 166(2):543-556, 1994.
Saito et al., *The Mechanism by Which Epidermal Growth Factor Inhibits Glycogen Synthase Kinase 3 in A431 Cells*, Biochemical Journal, 303(Part 1):27-31, 1994.
Mandelkow et al., *Tau as a Marker for Alzheimer's Disease*, TIBS, 18(12):480-483, 1993.
Van Der Linden et al., *Domain Organization of Penicillin-Binding Protein 5 from Escherichia coli Analysed by C-Terminal Truncation*, Biochemical Journal, 289(Part 2):593-598, 1993.
Welsh et al., *Glycogen Synthase Kinase-3 is Rapidly Inactivated in Response to Insulin and Phosphorylates Eukaryotic Initiation Factor eIF-2B*, Biochemical Journal, 294(Part 3):625-629, 1993.

(Continued)

*Primary Examiner*—Delia M. Ramirez
(74) *Attorney, Agent, or Firm*—Jane E. R. Potter; Young J. Suh; Alisa A. Harbin

(57) ABSTRACT

The invention provides truncated GSK3 polypeptides capable of crystallization, including GSK3α and GSK3β polypeptides, and use of these polypeptides to identify and optimize GSK3 inhibitors. Also provided are GSK3 polypeptides having at least one substituted amino acid that differs from wild-type GSK3, wherein the substituted amino acid is incapable of being phosphorylated. The invention finds use in providing methods of identifying and optimizing compounds useful for treating diseases mediated by GSK3 activity, including Alzheimer's disease, type 2 diabetes, and inflammation.

1 Claim, 10 Drawing Sheets

OTHER PUBLICATIONS

Jancarik et al.., *Sparse Matrix Sampling: A Screening Method for Crystallization of Proteins*, J. of Applied Crystallography, 24(4):409-411, 1991.

Woodgett, *A Common Denominator Linking Glycogen Metabolism, Nuclear Oncogenes and Development*, TIBS, 16(5):177-181, 1991.

Ranty et al., *Truncation of Ribulose-1, 5-Bisphosphate Carboxylase/Oxygenase (Rubisco) from Holoenzyme Assembly and Activity*, EMBO Journal, 9:1365-1373, 1990.

US 6,057,286, 05/2000, Harrison et al. (withdrawn)

* cited by examiner

FIGURE 1A

GSK-3β Sequence

| | | | | | | | | | | | | | |
|---|---|---|---|---|---|---|---|---|---|---|---|---|---|
|Met|Ser|Gly|Arg|Pro|Arg|Thr|Thr|Ser|Phe|Ala|Glu|Ser|Cys|Lys|Pro
1| | | |5| | | | |10| | | |15| |

Met Ser Gly Arg Pro Arg Thr Thr Ser Phe Ala Glu Ser Cys Lys Pro
1           5                   10              15

Val Gln Gln Pro Ser Ala Phe Gly Ser Met Lys Val Ser Arg Asp Lys
            20                  25              30

Asp Gly Ser Lys Val Thr Thr Val Ala Thr Pro Gly Gln Gly Pro
        35              40              45

Asp Arg Pro Gln Glu Val Ser Tyr Thr Asp Thr Lys Val Ile Gly Asn
    50                  55              60

Gly Ser Phe Gly Val Val Tyr Gln Ala Lys Leu Cys Asp Ser Gly Glu
65              70              75                      80

Leu Val Ala Ile Lys Lys Val Leu Gln Asp Lys Arg Phe Lys Asn Arg
            85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
            245                 250                 255

Phe Pro Gly Asp Ser Gly Val Asp Gln Leu Val Glu Ile Ile Lys Val
            260                 265                 270

FIGURE 1B

Leu Gly Thr Pro Thr Arg Glu Gln Ile Arg Glu Met Asn Pro Asn Tyr
       275                  280                285

Thr Glu Phe Lys Phe Pro Gln Ile Lys Ala His Pro Trp Thr Lys Val
   290               295                300

Phe Arg Pro Arg Thr Pro Glu Ala Ile Ala Leu Cys Ser Arg Leu
305               310               315            320

Leu Glu Tyr Thr Pro Thr Ala Arg Leu Thr Pro Leu Glu Ala Cys Ala
           325               330           335

His Ser Phe Phe Asp Glu Leu Arg Asp Pro Asn Val Lys His Pro Asn
       340               345             350

Gly Arg Asp Thr Pro Ala Leu Phe Asn Phe Thr Thr Gln Glu Leu Ser
      355              360            365

Ser Asn Pro Pro Leu Ala Thr Ile Leu Ile Pro Pro His Ala Arg Ile
   370               375            380

Gln Ala Ala Ala Ser Thr Pro Thr Asn Ala Thr Ala Ala Ser Asp Ala
385               390              395           400

Asn Thr Gly Asp Arg Gly Gln Thr Asn Asn Ala Ala Ser Ala Ser Ala
          405              410              415

Ser Asn Ser Thr
       420

FIGURE 2A

GSK-3β 557 Construct Sequence

Met Glu Tyr Met Pro Met Glu Gly Gly Gly

Met Ser Gly Arg Pro Arg Thr Thr Ser Phe Ala Glu Ser Cys Lys Pro
1           5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65              70                  75                      80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
            115                 120                 125

Asn Leu Val Leu Asp Tyr Val Pro Glu Thr Val Tyr Arg Val Ala Arg
        130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
                180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
            245                 250                 255

FIGURE 2B

Phe Pro Gly Asp Ser Gly Val Asp Gln Leu Val Glu Ile Ile Lys Val
            260             265                 270

Leu Gly Thr Pro Thr Arg Glu Gln Ile Arg Glu Met Asn Pro Asn Tyr
        275             280                 285

Thr Glu Phe Lys Phe Pro Gln Ile Lys Ala His Pro Trp Thr Lys Val
    290             295                 300

Phe Arg Pro Arg Thr Pro Pro Glu Ala Ile Ala Leu Cys Ser Arg Leu
305             310             315                         320

Leu Glu Tyr Thr Pro Thr Ala Arg Leu Thr Pro Leu Glu Ala Cys Ala
            325                 330                     335

His Ser Phe Phe Asp Glu Leu Arg Asp Pro Asn Val Lys His Pro Asn
            340             345                 350

Gly Arg Asp Thr Pro Ala Leu Phe Asn Phe Thr Thr Gln Glu Leu Ser
        355             360                 365

Ser Asn Pro Pro Leu Ala Thr Ile Leu Ile Pro Pro His Ala Arg Ile
    370                 375             380

FIGURE 3A

GSK-3β 580 Construct Sequence

Met Glu Tyr Met Pro Met Glu Gly Gly Gly

Gly Ser Lys Val Thr Thr Val Val Ala Thr Pro Gly Gln Gly Pro
    35                40                    45

Asp Arg Pro Gln Glu Val Ser Tyr Thr Asp Thr Lys Val Ile Gly Asn
50                    55                   60

Gly Ser Phe Gly Val Val Tyr Gln Ala Lys Leu Cys Asp Ser Gly Glu
65                   70                75                   80

Leu Val Ala Ile Lys Lys Val Leu Gln Asp Lys Arg Phe Lys Asn Arg
                85                90                95

Glu Leu Gln Ile Met Arg Lys Leu Asp His Cys Asn Ile Val Arg Leu
            100              105              110

Arg Tyr Phe Phe Tyr Ser Ser Gly Glu Lys Lys Asp Glu Val Tyr Leu
       115               120              125

Asn Leu Val Leu Asp Tyr Val Pro Glu Thr Val Tyr Arg Val Ala Arg
130                   135                  140

His Tyr Ser Arg Ala Lys Gln Thr Leu Pro Val Ile Tyr Val Lys Leu
145                  150                155              160

Tyr Met Tyr Gln Leu Phe Arg Ser Leu Ala Tyr Ile His Ser Phe Gly
            165              170              175

Ile Cys His Arg Asp Ile Lys Pro Gln Asn Leu Leu Leu Asp Pro Asp
          180              185              190

Thr Ala Val Leu Lys Leu Cys Asp Phe Gly Ser Ala Lys Gln Leu Val
          195              200              205

Arg Gly Glu Pro Asn Val Ser Tyr Ile Cys Ser Arg Tyr Tyr Arg Ala
210                   215                220

Pro Glu Leu Ile Phe Gly Ala Thr Asp Tyr Thr Ser Ser Ile Asp Val
225                  230              235              240

Trp Ser Ala Gly Cys Val Leu Ala Glu Leu Leu Leu Gly Gln Pro Ile
            245              250              255

Phe Pro Gly Asp Ser Gly Val Asp Gln Leu Val Glu Ile Ile Lys Val
          260              265              270

Leu Gly Thr Pro Thr Arg Glu Gln Ile Arg Glu Met Asn Pro Asn Tyr
       275               280              285

FIGURE 3B

Thr Glu Phe Lys Phe Pro Gln Ile Lys Ala His Pro Trp Thr Lys Val
    290                295                300

Phe Arg Pro Arg Thr Pro Pro Glu Ala Ile Ala Leu Cys Ser Arg Leu
305                310                315            320

Leu Glu Tyr Thr Pro Thr Ala Arg Leu Thr Pro Leu Glu Ala Cys Ala
              325              330              335

His Ser Phe Phe Asp Glu Leu Arg Asp Pro Asn Val Lys His Pro Asn
          340              345              350

Gly Arg Asp Thr Pro Ala Leu Phe Asn Phe Thr Thr Gln Glu Leu Ser
      355              360              365

Ser Asn Pro Pro Leu Ala Thr Ile Leu Ile Pro Pro His Ala Arg Ile
    370              375              380

FIGURE 4

Human GSK3α

```
MSGGGPSGGG PGGSGRARTS SFAEPGGGGG GGGGGPGGSA SGPGGTGGGK
1                                                    50
ASVGAMGGGV GASSSGGGPG GSGGGGSGGP GAGTSFPPPG VKLGRDSGKV
51                                                  100
TTVVATLGQG PERSQEVAYT DIKVIGNGSF GVVYQARLAE TRELVAIKKV
101                                                 150
LQDKRFKNRE LQIMRKLDHC NIVRLRYFFY SSGEKKDELY LNLVLEYVPE
151                                                 200
TVYRVARHFT KAKLTIPILY VKVYMYQLFR SLAYIHSQGV CHRDIKPQNL
201                                                 250
LVDPDTAVLK LCDFGSAKQL VRGEPNVSYI CSRYYRAPEL IFGATDYTSS
251                                                 300
IDVWSAGCVL AELLLGQPIF PGDSGVDQLV EIIKVLGTPT REQIREMNPN
301                                                 350
YTEFKFPQIK AHPWTKVFKS RTPPEAIALC SSLLEYTPSS RLSPLEACAH
351                                                 400
SFFDELRCLG TQLPNNRPLP PLFNFSAGEL SIQPSLNAIL IPPHLRSPAG
401                                                 450
TTTLTPSSQA LTETPTSSDW QSTDATPTLT NSS
451                                         483
```

FIGURE 5

Human GSK3α

```
MSGGGPSGGG PGGSGRARTS SFAEPGGGGG GGGGGPGGSA SGPGGTGGGK
1                                                   50
ASVGAMGGGV GASSSGGGPG GSGGGGSGGP GAGTSFPPPG VKLGRDSGKV
51                                                 100
TTVVATLGQG PERSQEVAYT DIKVIGNGSF GVVYQARLAE TRELVAIKKV
101                                                150
LQDKRFKNRE LQIMRKLDHC NIVRLRYFFY SSGEKKDELY LNLVLEYVPE
151                                                200
TVYRVARHFT KAKLTIPILY VKVYMYQLFR SLAYIHSQGV CHRDIKPQNL
201                                                250
LVDPDTAVLK LCDFGSAKQL VRGEPNVSYI CSRYYRAPEL IFGATDYTSS
251                                                300
IDVWSAGCVL AELLLGQPIF PGDSGVDQLV EIIKVLGTPT REQIREMNPN
301                                                350
YTEFKFPQIK AHPWTKVFKS RTPPEAIALC SSLLEYTPSS RLSPLEACAH
351                                                400
SFFDELRCLG TQLPNNRPLP PLFNFSAGEL SIQPSLNAIL IPPHLRS
401
```

FIGURE 6

Human GSK3α

```
                                                              SGKV
                                                              100
TTVVATLGQG  PERSQEVAYT  DIKVIGNGSF  GVVYQARLAE  TRELVAIKKV
101                                                           150
LQDKRFKNRE  LQIMRKLDHC  NIVRLRYFFY  SSGEKKDELY  LNLVLEYVPE
151                                                           200
TVYRVARHFT  KAKLTIPILY  VKVYMYQLFR  SLAYIHSQGV  CHRDIKPQNL
201                                                           250
LVDPDTAVLK  LCDFGSAKQL  VRGEPNVSYI  CSRYYRAPEL  IFGATDYTSS
251                                                           300
IDVWSAGCVL  AELLLGQPIF  PGDSGVDQLV  EIIKVLGTPT  REQIREMNPN
301                                                           350
YTEFKFPQIK  AHPWTKVFKS  RTPPEAIALC  SSLLEYTPSS  RLSPLEACAH
351                                                           400
SFFDELRCLG  TQLPNNRPLP  PLFNFSAGEL  SIQPSLNAIL  IPPHLRSPAG
401                                                           450
TTTLTPSSQA  LTETPTSSDW  QSTDATPTLT  NSS
451                                              483
```

FIGURE 7

Human GSK3α

```
                                                                  SGKV
                                                                   100
     TTVVATLGQG PERSQEVAYT DIKVIGNGSF GVVYQARLAE TRELVAIKKV
     101                                                            150
     LQDKRFKNRE LQIMRKLDHC NIVRLRYFFY SSGEKKDELY LNLVLEYVPE
     151                                                            200
     TVYRVARHFT KAKLTIPILY VKVYMYQLFR SLAYIHSQGV CHRDIKPQNL
     201                                                            250
     LVDPDTAVLK LCDFGSAKQL VRGEPNVSYI CSRYYRAPEL IFGATDYTSS
     251                                                            300
     IDVWSAGCVL AELLLGQPIF PGDSGVDQLV EIIKVLGTPT REQIREMNPN
     301                                                            350
     YTEFKFPQIK AHPWTKVFKS RTPPEAIALC SSLLEYTPSS RLSPLEACAH
     351                                                            400
     SFFDELRCLG TQLPNNRPLP PLFNFSAGEL SIQPSLNAIL IPPHLRS
     401
```

GSK3 POLYPEPTIDES

CROSS REFERENCE TO RELATED APPLICATIONS

This application is a divisional application of U.S. patent application Ser. No. 10/211,412 filed Jul. 31, 2002 now U.S. Pat. No. 6,716,624, which is a divisional application of U.S. patent application Ser. No. 09/916,109 filed Jul. 25, 2001 now U.S. Pat. No. 6,465,231, which claims the benefit of U.S. Provisional Patent Application No. 60/221,242 filed Jul. 27, 2000, where this provisional application is incorporated herein by reference in its entirety.

BACKGROUND OF THE INVENTION

1. Field of the Invention

The invention provides materials and methods relating to identification and optimization of selective inhibitors of glycogen synthase kinase 3 (GSK3), and also relates to methods of treating a condition mediated by GSK3 activity. Such conditions include Alzheimer's disease, type 2 diabetes, and inflammation.

2. Description of the Related Art

Glycogen synthase kinase 3 (GSK3) is a proline-directed serine/threonine kinase originally identified as an activity that phosphorylates glycogen synthase as described in Woodgett, *Trends Biochem Sci.* 16:177–181 (1991). The role in glucose metabolism has been elaborated recently in Summers et al., *J. Biol. Chem.* 274:17934–17940 (1999). GSK3 consists of two isoforms, α and β, and is constitutively active in resting cells, inhibiting glycogen synthase by direct phosphorylation. Upon insulin activation, GSK3 is inactivated, thereby allowing the activation of glycogen synthase and possibly other insulin-dependent events. GSK3 is inactivated by other growth factors or hormones that, like insulin, signal through receptor tyrosine kinases. Examples of such signaling molecules include IGF-1 and EGF as described in Saito et al., *Biochem. J.* 303:27–31 (1994), Welsh et al., *Biochem. J.* 294:625–629 (1993), and Cross et al., *Biochem. J.* 303:21–26 (1994). GSK3 has been shown to phosphorylate β-catenin as described in Peifer et al., *Develop. Biol.* 166:543–56 (1994). Other activities of GSK3 in a biological context include GSK3's ability to phosphorylate tau protein in vitro as described in Mandelkow and Mandelkow, *Trends in Biochem. Sci.* 18:480–83 (1993), Mulot et al., *Febs Lett* 349: 359–64 (1994), and Lovestone et al., *Curr. Biol.* 4:1077–86 (1995), and in tissue culture cells as described in Latimer et al., *Febs Lett* 365:42–6 (1995). Selective inhibition of GSK3/may be useful to treat or inhibit disorders mediated by GSK3 activity.

There is a need in the art for compositions and molecules that bind to or interact with GSK3, thereby mediating GSK3 activity. The invention meets this need by providing crystallizable GSK3 polypeptides useful for design and optimization of GSK3 inhibitors.

BRIEF SUMMARY OF THE INVENTION

The invention provides GSK3β molecules with N- and C-terminal truncations, wherein the molecules are capable of crystallization.

The invention further provides GSK3β molecules truncated at amino acid $R^{344}$, $R^{354}$, $T^{364}$, $A^{374}$, and $I^{384}$.

The invention provides a polypeptide consisting essentially of SEQ ID NO:2 or SEQ ID NO:3, polynucleotides encoding these polypeptides, and vectors comprising these polynucleotides.

The invention still further provides GSK3β molecules wherein translation of the molecule begins at $G^{34}$, $T^{39}$, $P^{44}$, $D^{49}$ or $V^{54}$.

The invention also provides GSK3α molecules with N- and C-terminal truncations, wherein the molecules are capable of crystallization.

The invention further provides a GSK3α molecule wherein translation of the molecule begins at $S^{97}$ and ends at $S^{447}$, polynucleotides encoding this polypeptide, and vectors comprising these polynucleotides.

The invention further provides a method of identifying a GSK3 polypeptide capable of crystallization, comprising: (a) providing a truncated GSK3 polypeptide; (b) testing the polypeptide for formation of crystals.

The invention also provides GSK3 polypeptides capable of interacting with inhibitors of GSK3.

The invention further provides a method of identifying an enzymatically active GSK3 polypeptide, comprising: (a) providing a truncated GSK3 polypeptide; (b) contacting the polypeptide with a substrate of GSK3; and (c) measuring the kinase activity of the polypeptide after contacting the polypeptide with the substrate, wherein the polypeptide is active if it shows >0.01× the activity of the full-length enzyme and preferably >0.1× the activity of the full-length enzyme.

BRIEF DESCRIPTION OF THE DRAWINGS AND SEQUENCE IDENTIFIERS

FIG. 1 provides the polypeptide sequence of human GSK3β (SEQ ID NO:1).

FIG. 2 provides the polypeptide sequence of truncated GSK3β polypeptide 557 (SEQ ID NO:2). The first ten amino acids represent a Glu-tag, followed by a Gly linker before Met at position 1.

FIG. 3 provides the polypeptide sequence of truncated GSK3β polypeptide 580 (SEQ ID NO:3). The first ten amino acids represent a Glu-tag, followed by a Gly linker before Gly at position 34.

FIG. 4 provides the polypeptide sequence of human GSK3α (SEQ ID NO:4).

FIG. 5 provides the polypeptide sequence of human GSK3α truncated at position 447 (SEQ ID NO:5).

FIG. 6 provides the polypeptide sequence of human GSK3α truncated at position 97 (SEQ ID NO:6).

FIG. 7 provides the polypeptide sequence of human GSK3α from position 97 to position 447 (SEQ ID NO:7).

DETAILED DESCRIPTION OF THE INVENTION

The invention provides materials and methods for identifying and optimizing inhibitors of GSK3, including GSK3α and GSK3β. The provided materials include C- and N-terminal truncated GSK3β molecules that are capable of crystallization and may, but need not, retain GSK3 kinase activity, preferably more than 0.01× the activity of the full-length enzyme and more preferably more than 0.1× the activity of the full-length enzyme. There is a need in the art for such inhibitors, in view of the role of GSK3 in a variety of diseases and conditions, including Alzheimer's disease, type 2 diabetes and inflammation. Such inhibitors can be identified, and identified inhibitors can be optimized, using the crystallizable GSK3 polypeptides of the invention.

The invention provides a variety of GSK3β polypeptides that differ from the native polypeptide at the C- and/or N-terminus. The amino acid sequence of GSK3β is shown in FIG. 1 (SEQ ID NO:1). Included within the scope of the invention are any and all truncations of GSK3β polypeptide wherein the truncated polypeptide is capable of crystallization and may, but need not, retain kinase activity as measured using the kinase assays described herein. Persons of skill in the art will realize that limited mutation of the protein, or certain post-translational modifications, might be sufficient to inactivate the kinase yet retain the essential 3D structure. Such inactive but structurally related molecules would also be useful for the design and optimization of inhibitors. Kinase assays are disclosed in U.S. Pat. Nos. 6,057,117 and 6,057,286, which are incorporated herein by reference. The percent activity that is retained, if any, is not crucial. Methods of assaying activity in the presence and absence of an inhibitor are described herein.

The invention provides numerous truncated GSK3β polypeptides that meet these criteria. A preferred polypeptide is designated BV557 in which the C-terminal amino acid is $R^{384}$. This molecule has been successfully crystallized. Additional active polypeptides include those with truncations at amino acid $R^{344}$, $R^{354}$, $A^{374}$, and $I^{384}$.

The invention also provides truncated GSK3α polypeptides, including a GSK3α polypeptide beginning at $S^{97}$ and ending at $S^{447}$.

Additional truncated GSK3 polypeptide include those beginning with an N-terminal amino acid that differs from that of the native protein in that 1 or more amino acids are deleted from the N-terminus. Preferred N-terminal truncations include GSK3β molecules wherein translation of the molecule begins at $G^{34}$, $T^{39}$, $P^{44}$, $D^{49}$ or $V^{54}$. An example is BV580 (amino acids 34 to 384) which has been crystallized.

The invention is not limited to these disclosed truncated molecules. Using the methods and assays described herein, one of skill can construct additional truncated molecules, such as those having 36–76 amino acids deleted from the C-terminus, and/or 35–54 amino acids deleted from the N-terminus. Such deletions can occur individually, or a polypeptide can have both an N-terminal deletion and a C-terminal deletion. It is preferable but not necessary that the kinase domain remain relatively intact as reflected by the detection of enzymatic activity, such as by using the assays described herein. It is also desirable, although not essential, that the enzymatic activity be capable of inhibition by a known GSK3 inhibitor, such as lithium. A truncated molecule meeting these criteria will be suitable for testing GSK3 inhibitors as potential therapeutic agents, and for optimizing GSK3 inhibitors.

A truncated GSK3β polypeptide of the invention can consist of between about 250 and 419 contiguous amino acids of SEQ ID NO:1; preferably between about 278 and 419 contiguous amino acids of SEQ ID NO:1; more preferably between about 285 and 384 contiguous amino acids of SEQ ID NO:1; and most preferably between about 351 and 384 contiguous amino acids of SEQ ID NO:1. Preferred truncated GSK3β polypeptides include those beginning at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 of SEQ ID NO:1, and ending at amino acid 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418 or 419 of SEQ ID NO:1. The polypeptide can begin with any one of the listed beginning amino acids and end with any one of the ending amino acids. Exemplary and non-limiting embodiments begin at amino acid 34, 39, 44 or 54 and end at amino acid 420. Other particularly preferred embodiments begin at about amino acid 1 and end at amino acid 340, 344, 354, 374, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, or 420.

The truncated GSK3α polypeptide of the invention can consist of between about 182 and 482 contiguous amino acids of SEQ ID NO:4, preferably between about 182 and 386 contiguous amino acids of SEQ ID NO:4, more preferably between about 182 and 351 contiguous amino acids of SEQ ID NO:4, and most preferably from about $S^{97}$ to $S^{447}$ of SEQ ID NO:4.

The truncated GSK3 polypeptides can be prepared by any method known in the art. One method involves expression of a suitably prepared polynucleotide encoding a polypeptide having the desired truncation. For example, a preferred polypeptide of the invention, BV557, was prepared by creating a construct encoding GSK3β starting at $M^1$ and ending at $I^{384}$, as described in the Examples. Briefly, insect cells were transfected with baculovirus vector (designated pBlueBac4.5.Glu.GSK3B.DC.I384#28), which encodes BU557, and the protein was extracted from the lysed cells. The protein was purified by affinity chromatography using an anti glu-tag monoclonal antibody immobilized on a Sepharose column. Activity of the purified protein was assayed using the in vitro kinase assay described in U.S. Pat. No. 6,057,286.

The Examples herein describe the production of BV557, BV580, and other truncated GSK3 polypeptides by expression of vectors encoding the polypeptides, followed by isolation and purification of the polypeptides. The polypeptide can also be produced by enzymatic cleavage of a native GSK3 protein, using methods known in the art. Other suitable methods include expression of a polynucleotide encoding a truncated polypeptide in a variety of cell types, including mammalian, bacterial, or yeast cells. However, the preferred cell for expression of the polypeptide is an insect cell, preferably a baculovirus-infectable insect cell, such as a Sf9 cell.

The invention also provides unphosphorylated forms of GSK3 wherein the ATP binding site is identical to that of the wild-type protein. Such forms include Y216 non-phosphorylated GSK3β and Y279 non-phosphorylated GSK3α. Other forms include constructs with at least one amino acid change that prevents phosphorylation, such as GSK3β in which Y216 is changed to F216, and GSK3α in which Y279 is changed to F279. These forms are suitable for inhibitor binding assays to identify inhibitors of GSK3. The invention provides a GSK3β molecule in which position 216 is not phosphorylated. We have demonstrated that a GSK3β peptide with Y216 mutated to F216 crystalized and exhibits a structure in which the ATP-binding site is not substantially different from the un-mutated peptide.

Additional single and multiple amino acid changes include $S^9$ to $A^9$ in GSK3β and $S^{21}$ to $A^{21}$ in GSK3α.

These changes in phosphorylation, or ability to be phosphorylated, are optionally incorporated into the truncated forms of GSK3α and GSK3 β disclosed herein.

The invention therefore provides GSK3 molecules suitable for design and optimization of inhibitors of GSK3 as pharmaceutical agents.

The GSK3 constructs of the invention are capable of crystallization. In purified form the constructs bind to inhibitors in a manner that is comparable to inhibitor binding to the native GSK3 polypeptide, due to the retention of the correct folding conformation at the inhibitor binding site. Potential to crystallize is measured using a variety of assays including specific activity, aggregation, microheterogeneity. (See, for example, Table 1). These parameters are indicative of the purity of the preparation and of the solubility of the construct. The specific activity is also a preferred assay for detecting binding of an inhibitor to the correct binding site of the GSK3 construct. Another suitable method is fluorescence polarization. Briefly, a putative inhibitor, with an attached fluorophore, tumbles freely in solution. Thus when the fluorophore is excited by polarized light, the emitted light which is produced after a finite delay now has random polarity and the emitted light is no longer polarized. In the presence of a GSK3 construct with an intact inhibitor binding site, the tumbling rate is slowed sufficiently to ensure that, even though the light emission is delayed with respect to the excitation, the fluorophore has only moved very slightly. Thus, the excited light maintains polarization. A measurement of fluorescence polarization therefore indicates whether or not the GSK3 construct is suitable for identifying and optimizing an inhibitor. The fluorophore can be attached to a compound such as staurosporine (ICN Pharmaceuticals, Inc., Costa Mesa, Calif.). GSK3 constructs may not retain kinase activity, but their inhibitor binding can still be assessed using fluorescence polarization assays.

The term "truncated glycogen synthase kinase 3" or "truncated GSK3" as used herein refers to GSK3α or GSK3β. GSK3 is a protein originally identified by its phosphorylation of glycogen synthase as described in Woodgett et al, *Trends Biochem Sci,* 16:177–181 (1991). Synonyms of GSK3 are tau protein kinase I (TPK I), FA kinase and kinase FA. Mammalian forms of GSK3 have been cloned as described in Woodgett, *EMBO J.* 9(8): 2431–2438 (1990). Inhibitors of truncated GSK3 polypeptides can be inhibitors of any of the known forms of GSK3, including either GSK3α or GSK3β or both. Truncated polypeptides of the invention possess one or more of the bioactivities of the GSK3 protein, including kinase activities such as polymerizing tau protein, or phosphorylating glycogen synthase, for example. Thus, truncated GSK3 polypeptides useful for designing and optimizing inhibitors of GSK3 can have sequence identity of at least 40%, preferably 50%, preferably 60%, preferably 70%, more preferably 80%, and most preferably 90% to the amino acid sequence of the native protein, wherever derived, from human or nonhuman sources. The polynucleotides encoding a GSK3 polypeptide can have 60%, preferably 70%, more preferably 80%, more preferably 90% and most preferably 95% sequence identity to a native polynucleotide sequence of GSK3. Also included, therefore, are alleles and variants of the native polynucleotide sequence such that the polynucleotide encodes an amino acid sequence with substitutions, deletions, or insertions, as compared to the native sequence.

The term "peptide substrate" refers to a peptide or a polypeptide or a synthetic peptide derivative that can be phosphorylated by GSK3 activity in the presence of an appropriate amount of ATP or a phosphate donor. Detection of the phosphorylated substrate is generally accomplished by the addition of a labeled phosphate that can be detected by some means common in the art of labeling, such as radiolabeled phosphate. The peptide substrate may be a peptide that resides in a molecule as a part of a larger polypeptide, or may be an isolated peptide designed for phosphorylation by GSK3.

As disclosed in U.S. Pat. Nos. 6,057,117 and 6,057,286, in vitro methods of assaying GSK3 activity include constructing peptide substrates. The peptide substrate can be any peptide substrate phosphorylatable by GSK3, and may be a peptide substrate including the formula: anchor ligand-$(X)_n$SXXXS$(X)_m$ (SEQ ID NO:11) (wherein X is any amino acid, n is any integer, m is any integer, and preferably n+m+5<20, i.e. n+m<15) prephosphorylated at the C terminal serine. The assay is performed by contacting the prephosphorylated substrate with truncated GSK3 polypeptide in the presence of radiolabeled γphosphate-ATP, a substrate anchor, and optionally a candidate inhibitor. The in vitro method of identifying an inhibitor of GSK3 kinase activity includes contacting a peptide substrate coupled to an anchor ligand with truncated GSK3 polypeptide in the presence of radiolabeled γphosphate-ATP, a substrate anchor, and candidate inhibitor, measuring an incorporation of radiolabel into the peptide substrate, then, in a separate assay vessel contacting a peptide substrate coupled to an anchor ligand with truncated GSK3 in the presence of radiolabeled γphosphate-ATP, and a substrate anchor, and measuring incorporation of radiolabel into said peptide substrate; ultimately an inhibitor of truncated GSK3 kinase activity is identified by a reduction of label incorporation in the assay with the candidate inhibitor as compared to the assay without the candidate inhibitor.

To conduct the in vitro kinase assay of the invention using microwells, scintillant may be present by pre-coating the wells with a scintillant material, or by adding it later following a wash step, as described in Example 4. The scintillant can be obtained from Packard, Meridian, Conn. Wells coated with scintillant are then in addition coated with streptavidin as a substrate anchor, where biotin is the anchor ligand on the peptide. Alternatively, the streptavidin can be present on agarose beads containing scintillant or may be coated on an otherwise untreated plate to which scintillant is added subsequently. In any event, the streptavidin in the wells binds the biotin that contacts it. Following an assay using radiolabeled ATP, the radiolabel incorporated into the phosphorylated substrate that has been conjugated to the biotin will cause the scintillant to emit light. Where the streptavidin is attached to agarose beads containing scintillant, binding a biotin-conjugated radiolabeled peptide substrate will cause the beads to scintillate. In both the case of the wells lined with the scintillant, and the agarose beads containing scintillant, a reduction in scintillation as compared to a control amount of scintillation measured under non-inhibitory conditions, indicates the presence of a functional inhibitor of GSK3 activity. If the peptide has been phosphorylated by GSK3 with $^{32}$P-labeled or $^{33}$P-labeled phosphate, radioactive decay will cause the scintillant present in a microwell or mixed in agarose beads that are present in the reaction mixture to emit light and the measure of the amount of light emitted will be a measure of the activity of GSK3 in the assay. Low activity of GSK3 observed in the presence of a candidate inhibitor, as compared to the activity of GSK3 in the absence of the inhibitor, may indicate that the inhibitor is functional and can inhibit GSK3 kinase activity. In any case, an excess of streptavidin over peptide should be loaded into each well or should be affixed to the agarose beads.

GSK3 inhibitory activity can be measured using a cell-free assay as disclosed in publication WO 99/65897, and as described in Example 4 herein. Activity can also be measured using a cell-based assay. Briefly, a cell line, such as a Cos cell line, is transfected with Tau and with a GSK3 polypeptide. The phosphorylation of Tau at a specific site is monitored using a monoclonal antibody, as phosphorylation at that site is dependent on GSK3 activity.

Exemplary polypeptides of the invention include the following truncated polypeptides with reference to SEQ ID NO:1:

GSK3β truncated at $R^{344}$
GSK3β truncated at $R^{354}$
GSK3β truncated at $T^{364}$
GSK3β truncated at $A^{374}$
GSK3β truncated at $I^{384}$
GSK3β beginning at $G^{34}$
GSK3β beginning at $T^{39}$
GSK3β beginning at $P^{44}$
GSK3β beginning at $D^{49}$
GSK3β beginning at $V^{54}$ The above truncations can be combined, providing a GSK3β polypeptide beginning at any of $G^{34}$, $T^{39}$, $P^{44}$, $D^{49}$, or $V^{54}$, and ending at any of $R^{344}$, $R^{354}$, $T^{364}$, $A^{374}$, or $I^{384}$.

Other exemplary polypeptides of the invention include the following truncated polypeptides with reference to SEQ ID NO:4:

GSK3α truncated at $S^{447}$.
GSK3α beginning at $S^{97}$.
GSK3α beginning at $S^{97}$ and truncated at $S^{447}$.

A truncated GSK3 polypeptide of the invention can be selected on the basis of one or more parameters. A polypeptide will preferably crystallize in a form that is similar to that of native GSK3, with correct folding at and around the inhibitor binding site. Crystallization can be performed using a Crystal Screen Kit (Hampton Research, Laguna Niguel, Calif.), or methods described by Jancarik, J. et al., *J. Appl. Cryst.* 24:409–411, 1991. The potential of a polypeptide to form crystals can be evaluated on the basis of specific activity, purity, homogeneity, mass spectrometry, aggregation, and dynamic light scattering. A preferred truncated polypeptide will meet the following parameters: purity of at least 90%; less than 100% aggregation at 4° C. at two weeks; and less than 50% heterogeneity (50% or greater of the desired form). A most preferred truncated polypeptide will have a purity of at least 98%, no aggregation at 4° C. at two weeks; and less than 5% heterogeneity (unphosphorylated form). Such parameters indicate that the polypeptide preparation is likely to crystallize, making it suitable for discovering and optimizing GSK3 inhibitors.

A prerequisite for crystallization is to obtain a sufficiently concentrated stock of protein. Not all GSK3 constructs will remain soluble at the required concentration. A preferred concentration is >1 mg/ml, more preferred is >5 mg/ml, and most preferred is >10 mg/ml.

The polypeptides disclosed herein as 557 (SEQ ID NO:2), 580 (SEQ ID NO:3), 458, and 524 meet the criteria described above (see Example 3). Polypeptide 458 consists of amino acids 1–420 of SEQ ID NO:1 plus the following addition at the N-terminus: EFMPTEAMAAPKRVI (SEQ ID NO:8). Polypeptide 524 consists of amino acids 1–420 of SEQ ID NO:1 plus the following addition at the N-terminus: EYMPMEGGG (SEQ ID NO:9). Other modified or truncated GSK3 polypeptides can be prepared and tested as described herein.

EXAMPLES

The following examples are exemplary only, and are not intended to limit the invention.

Example 1

Preparation and Purification of GSK3β Construct 557

Lysis and Extraction. Insect cell slurry from Sf9 cells (about 10 g) from a 1 liter flask growth was combined with 30 ml of lysate buffer: 20 mM Tris, pH 8.0/80 mM NaCl/1 mM $MgCl_2$/1 mM Arsenate/1 mM Tungstenate/1 mM PMSF/0.5 mg Leupeptin/0.2 mg Aprotinin. Cells were lysed using a Dounce homogenizer. Improved extraction of the protein was accomplished by the addition of 5% glycerol and 0.2% octylglucoside. The mixture was allowed to stir, on ice, for 30 minutes. The total lysate was centrifuged at 39000×g for 25 minutes at 4° C. The resulting supernatant contained the extracted GSK3-β #557.

Ion Exchange Chromatography. The following materials and conditions were used: The resin was Fractogel EMD $SO_3$— (M); the column diameter was 1.6 cm and the column volume was 10 ml. The column was run at a flowrate of 90 cm/hour using equilibration buffer of 20 mM Na Phosphate/5% Glycerol, pH 7.5. Chromatography was carried out at 4° C.

The lysate supernatant was diluted 1:1 with S-fractogel equilibration buffer, and loaded onto the equilibrated column. The column was washed with a total of 14 column volumes of equilibration buffer. The GSK3-β was eluted with a linear salt gradient, over 20 column volumes, to equilibration buffer plus 1M NaCl. 3 ml/fraction was collected during gradient elution. The pool was made based on SDS-PAGE and Western blot results of the fractions collected. Fractions 13–24 were pooled.

Affinity Chromatography was performed using the following materials and procedures: The resin was anti glu-tag monoclonal antibody immobilized onto Protein G Sepharose, and the equilibration buffer was PBS/0.3M NaCl/0.2% octylglucoside/10% Glycerol. The column diameter was 1.6 cm and the column volume was 13 ml. The flow rate was 30 cm/hour during load and wash, and 15 cm/hour during elution.

The S-Fractogel pool was loaded at 30 cm/hour onto equilibrated column. The column was washed down to absorbance baseline with approximately 6 column volumes of equilibration buffer, and GSK3β was eluted with 50 ml of equilibration buffer containing 2 mg of elution peptide (EYMPTD)(SEQ ID NO:10). The flow rate during elution was lowered to 15 cm/hour. 2 ml/fractions were collected during the elution. Based on SDS-PAGE results, elution fractions 6–17 were pooled with a total volume of 24 ml.

Final Yield. The affinity column pool, at a concentration of 0.17 mg/ml, contained 4.1 mg of GSK3β #557. This translates to a final yield of 4.1 mg purified 557/liter of growth. Purity, after this 2 column purification, was estimated at >95% by visual inspection of SDS-PAGE results.

Example 2

Preparation and Purification of GSK3β Construct 580

Extraction. SF9 cell paste from a 10 L fermentation was washed with 100 mL PBS (10 mM NaPi, pH7.5, 150 mM NaCl) and then resuspended with 300 mL of Buffer H (20 mM Tris, pH 7.5, 1 mM Tungstate, 1 mM Arsenate, 5 mM DTT, 10 µg/mL Leupeptin, 1 µg/mL pepstatin A, 10% glycerol, 0.35% Octyl glucoside, 1 mM $Mg^{2+}$). Cells were homogenized in a 100-mL Dounce Homogenizer (20 strokes with pestle B). The combined homogenate was centrifuged in a Ti45 rotor at 40,000 rpm for 35 minutes to remove cell debris and nuclei. The supernatant from the centrifugation were carefully decanted and filtered through 0.45µ filter.

S-Fractogel. 100 mL S-Fractogel (EM Science, Cat #18882) was packed into a 3.2 cm×12.5 cm column and equilibrated with >1 L of buffer A (20 mM Tris, pH 7.5, 10% glycerol). The filtrate from the previous step was loaded at 15 mL/min onto the column. The column was washed with 1 L of buffer A and then eluted with a linear gradient from 0 to 1 M NaCl in buffer A over 20 column volumes. The eluant was fractionated into 20 mL each. Fractions containing GSK3 were detected by Western Blot using anti-GSK antibody (Santa Cruz Biotech, Cat # SC-7291). The Western-Blot positive fractions were pooled and mixed with equal volume of buffer M (20 mM Tris, pH 7.5, 10% glycerol, 3.1 M NaCl) and filtered through a 0.45µ filter. The filtrate was saved for Phenyl-650 M chromatography.

al., *Anal. Biochem.*, 220:397–402 (1994))µ in reaction buffer (5 mM Tris, pH 7.5, 5 mM DTT; 1 mM MgCl2, 0.01% BSA) containing the desired amount of truncated GSK3 polypeptide. ATP was added (specific activity 5.3 Ci/mmol) to 25 µM final concentration and the mixture was incubated for 20 min. at room temperature. The reaction was stopped by transferring 30 µl onto a P81 filter disc (Whatman). The disc was washed four times in 150 ml of 75 mM $H_3PO_4$ for 5 minute each. The filter was air dried and counted under 5 ml scintillation fluid. The specific activity was counted by determining the ratio of counts (in cpm) by the mass of GSK3 in the reaction (in µg).

The specific activity for construct 557 was $4.3 \times 10^7$ cpm/µg; for construct 458, $2.8 \times 10^7$ cpm/µg; and for construct 524, $2.2 \times 10^7$ cpm/µg.

TABLE 1

| Construct | Purity | Mean Specific Activity cpm/µg | N | Concentration mg/ml | Aggregation at 4 Degrees | Aggregation at RT | Heterogeneity |
|---|---|---|---|---|---|---|---|
| 458 | >98% | $2.8 \times 10^7$ | 35 | 11.5 | 11% @ > 2 weeks | overnight | 10–20% unphosphorylated |
| 557 | >98% | $4.3 \times 10^7$ | 7 | 12.7 | none @ > 2 weeks | overnight | 5% unphosphorylated |
| 524 | >98% | $2.2 \times 10^7$ | 24 | 10 | ND | | <5% unphosphorylated |

N = number of assays used to determine "mean specific activity."

Phenyl-650 M. 37.5 mL Phenyl-650 M (Tosohass, Cat # 014943) was packed into a 2.2×10 cm column and equilibrated with 500 mL of buffer C (20 mM Tris, pH 7.5, 10% glycerol, 1.6 M NaCl). Filtrate from S-fractogel step was loaded onto the column at 7.5 mL/min. After the loading was completed, the column was washed with 6.5 cv buffer C and eluted with a linear gradient from 0% to 100% Buffer D (20 mM Tris, pH 7.5, 10% glycerol) over 20 column volumes. Fractions were collected at 15 mL each and GSK containing fractions were detected by Western Blot using anti-GSK antibody. The Western positive fractions were pooled and loaded onto a Glu-tag antibody affinity column.

Glu-tag antibody Affinity Chromatography. Use of a Glu-tag is described in Rubinfeld et al., *Cell* 65:1033–1042, 1991, and a hybridoma expressing anti-Glu-tag antibody is described in Grussenmyer et al., *PNAS* 82:7952–7954 (1985). 50 mg of the Glu-tag antibody was immobilized onto 25 mL of Affi-Gel 10 (BioRAD, Cat #153–6046) and packed into a 2.2×6.5 cm column. The column was equilibrated with 200 mL of buffer E (20 mM Tris, pH 7.5, 10% glycerol, 0.3 M NaCl, 0.2% Octylglucoside) and the fraction pool from the Phenyl-650 M step was loaded at 1.0 mL/min. After the loading was completed, the column was washed with 100 mL of buffer E and then eluted with 60 mL Glu-tag peptide (100 µg/mL) in Buffer E and fractionated into 5 mL each. GSK containing fractions were detected with SDS-PAGE and Coomassie Blue staining. These fractions were pooled and concentrated to approximately 6 mg/mL in an Amicon concentrator using a 10 k MWCO YM10 membrane. The concentrated material was then ready for crystallization.

Example 3

Activity of Truncated GSK3β Polypeptides

A reaction mixture was prepared containing 5.9 µM prephosphorylated SGSG-linked CREB peptide (Wang et Example 4

Screening for GSK3 Inhibitory Activity Using a Cell-Free Assay

Compounds to be tested as GSK3 inhibitors are dissolved in DMSO, then tested for inhibition of human GSK3β. Expression of GSK3β is described, for example, in Hughes et al., *Eur. J. Biochem.*, 203:305–11 (1992), which is incorporated herein by reference. An aliquot of 300 µl of substrate buffer (30 mM tris-HCl, 10 mM $MgCl_2$, 2 mM DTT, 3 µg/ml GSK3β) and 0.5 µM biotinylated prephosphorylated SGSG-linked CREB peptide (Chiron Technologies PTY Ltd., Clayton, Australia) is dispensed into wells of a 96 well polypropylene microtiter plate. 3.5 µl/well of DMSO containing varying concentrations of each compound to be assayed or staurosporine (a known kinase inhibitor used as a positive control, or a negative control) (i.e., DMSO only), is added and mixed thoroughly. The reactions is then initiated by adding 50 µl/well of 1 µM unlabeled ATP and $1-2 \times 10^7$ cpm $\gamma^{33}P$-labeled ATP, and the reaction is allowed to proceed for about three hours at room temperature.

While the reaction is proceeding, streptavidin-coated Labsystems "Combiplate 8" capture plates (Labsystems, Helsinki, Finland) are blocked by incubating them with 300 µl/well of PBS containing 1% bovine serum albumin for at least one hour at room temperature. The blocking solution is then removed by aspiration, and the capture plates are filled with 100 µl/well of stopping reagent (50 µM ATP/20 mM EDTA).

When the three hour enzyme reaction is finished, triplicate 100 µl aliquots of each reaction mix are transferred to three wells containing stopping solution, one well on each of the three capture plates, and the well contents are mixed well. After one hour at room temperature, the wells of the capture plates are emptied by aspiration and washed five times using PBS and a 12 channel Corning 430474 ELISA plate washer. Finally, 200 μl of Microscint-20 scintillation fluid is added to each well of the plate. The plates are coated with plate sealers, then left on a shaker for 30 minutes. Each capture plate is counted in a Packard TopCount scintillation counter (Meridian, Conn.) and the results are plotted as a function of compound concentration.

Compounds identified using this method can be further optimized by testing their ability to bind to truncated GSK3 polypeptides of the invention, using the fluorescence polarization assay, for example, for truncated polypeptides that do not exhibit GSK3 kinase activity. Alternatively, a truncated GSK3 polypeptide of the invention can be used in place of the native GSK3 protein.

Example 5

Screening for Inhibition of TAU Protein Phosphorylation

A. Transient Transfection of COS Cells with Expression Plasmid Encoding Truncated GSK3 and Tau Expression Plasmid Construction COS cells are maintained in T25 tissue culture flasks in high glucose MEM medium/5% fetal bovine serum. Cells from a confluent T25 flask are harvested and 80,000 cells/well are seeded into Corning 6-well tissue culture plates in a final volume of 2 ml/well of medium. The cells are left to grow at 37° C. for 48 hours. The cells are then washed twice in Opti-MEM containing no fetal bovine serum, and finally the cells are left in 1 ml of Opti-MEM.

Polynucleotide encoding tau protein is subcloned into plasmid pSG5 under an early SV40 promoter to generate a tau expression plasmid. The cloning of cDNA encoding tau protein is generally described in Goedert et al., *EMBO Journal*, 8(2):393–399 (1989), which is incorporated herein by reference. A GSK3 expression plasmid is prepared by subcloning polynucleotide encoding truncated GSK3 into pCG, which is an ApEVRF derivative described in Giese et al., *Genes & Development*, 9:995–1008 (1995) and Matthias et al., *Nucleic Acid Research*, 17:6418 (1989), both of which are incorporated herein by reference. The polynucleotide can encode any of the truncated GSK3 polypeptides of the invention.

The following solutions are prepared in 1.5 ml Eppendorf tubes:

Solution A: for each transfection, 2 μg of DNA (tau expression plasmid) and 0.7 μg of DNA (GSK3 expression plasmid) are diluted into 100 μl of Opti-MEM (Gibco BRL); Solution B: for each transfection, 8 μl of Lipofectamine reagent is diluted into 100 μl of Opti-MEM. The two solutions are combined, mixed gently, and incubated at room temperature for 45 minutes to allow DNA-liposome complexes to form. For each transfection, 0.8 ml of Opti-MEM is added to the tube containing the complexes. The diluted solution is mixed gently and overlaid onto the rinsed cells. The cells are incubated with the complexed DNA/Lipofectamine for 6 hours at 37° C. in a $CO_2$ incubator. Following incubation, 1 ml of growth medium (high glucose MEM) with 20% FBS is added to each well and incubated at 37° C. overnight. The medium is replaced with fresh, complete medium at 18 hours following the start of transfection, and the cells are left to grow at 37° C. for another 48 hours.

B. Tau Phosphorylation Inhibition Assay

Two hours before harvesting, 2 μl of GSK3 inhibitor dissolved in DMSO is added to each well and incubated at 37° C. After 2 hours the medium is removed and the cells are rapidly frozen on the plates on dry ice and stored at −70° C. Cells are thawed on ice in the presence of 200 μl of lysing buffer (1% Triton® X-100, 20 mM Tris pH 7.5, 137 mM NaCl, 15% glycerol, 25 μg/ml leupeptin, 1 μg ml pepstatin-A, 1 μM PMSF, 21 μg/ml aprotinin, 50 mM NaF, 50 mM β-glycerophosphate, 15 mM sodium pyrophosphate, 1 mM sodium orthovanadate). The contents of each well are centrifuged at 14,000 g, 4° C. for 5 minutes and the supernatants transferred to clean tubes. At this point the lysates may be stored at −20° C.

C. ELISA to Detect Phosphorylated Tau in Cell Lysates

Immulon 4 strips (Dynatech) are coated with monoclonal anti-phosphorylated tau (AT8, Polymedco, Inc.) at 5 μg/ml in PBS containing Ca++ and Mg++, 100 μl/well. After overnight incubation at 4° C., the strips are washed twice with washing buffer (PBS containing 0.05% Tween® 20) and blocked with PBS containing 1% BSA, 5% normal mouse serum and 0.05% Tween® 20 at room temperature for 1 hour. The strips are washed 5 times with washing buffer. Lysate (100 μl) diluted 1:10 in PBS containing 1% BSA, 0.1% $NaN_3$ is added into each well and incubated at room temperature for 1 hour. After washing, 100 μl of 0.5 μg/ml biotinylated monoclonal anti-(non-phosphorylated) tau (HT7, Polymedco, Inc.) in PBS-BSA is added into each well. Strips are washed 5 times and HRP-conjugated streptavidin is added, incubated at room temperature for 30 minutes and washed extensively with washing buffer. TMB substrate (Pierce) is used for color development and the reaction is stopped by adding an equal volume of 0.8 M sulfuric acid. Strips are read on an ELISA plate reader using a 450 nm filter. The concentration of compound that inhibits tau phosphorylation to 50% of the maximal level (i.e., $IC_{50}$) is determined by fitting a sigmoidal curve to the plotted data.

Those skilled in the art will recognize, or be able to ascertain, using not more than routine experimentation, many equivalents to the specific embodiments of the invention described herein. Such specific embodiments and equivalents are intended to be encompassed by the following claims.

All patents, published patent applications, and publications cited herein are incorporated by reference as if set forth fully herein.

The invention claimed is:

1. An isolated polypeptide consisting of the amino acid sequence of SEQ ID NO: 2.

* * * * *

SEQUENCE LISTING

<160> NUMBER OF SEQ ID NOS: 11

<210> SEQ ID NO 1
<211> LENGTH: 420

```
<212> TYPE: PRT
<213> ORGANISM: Homo sapiens

<400> SEQUENCE: 1

Met Ser Gly Arg Pro Arg Thr Thr Ser Phe Ala Glu Ser Cys Lys Pro
 1               5                  10                  15

Val Gln Gln Pro Ser Ala Phe Gly Ser Met Lys Val Ser Arg Asp Lys
                20                  25                  30

Asp Gly Ser Lys Val Thr Thr Val Ala Thr Pro Gly Gln Gly Pro
         35                  40                  45

Asp Arg Pro Gln Glu Val Ser Tyr Thr Asp Thr Lys Val Ile Gly Asn
 50                      55                  60

Gly Ser Phe Gly Val Val Tyr Gln Ala Lys Leu Cys Asp Ser Gly Glu
 65                  70                  75                  80

Leu Val Ala Ile Lys Lys Val Leu Gln Asp Lys Arg Phe Lys Asn Arg
                 85                  90                  95

Glu Leu Gln Ile Met Arg Lys Leu Asp His Cys Asn Ile Val Arg Leu
                100                 105                 110

Arg Tyr Phe Phe Tyr Ser Ser Gly Glu Lys Lys Asp Glu Val Tyr Leu
            115                 120                 125

Asn Leu Val Leu Asp Tyr Val Pro Glu Thr Val Tyr Arg Val Ala Arg
130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
            195                 200                 205

Arg Gly Glu Pro Asn Val Ser Tyr Ile Cys Ser Arg Tyr Tyr Arg Ala
            210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
            275                 280                 285

Thr Glu Phe Lys Phe Pro Gln Ile Lys Ala His Pro Trp Thr Lys Val
            290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys His Pro Asn
            340                 345                 350

Gly Arg Asp Thr Pro Ala Leu Phe Asn Phe Thr Thr Gln Glu Leu Ser
            355                 360                 365

Ser Asn Pro Pro Leu Ala Thr Ile Leu Ile Pro Pro His Ala Arg Ile
            370                 375                 380

Gln Ala Ala Ala Ser Thr Pro Thr Asn Ala Thr Ala Ala Ser Asp Ala
385                 390                 395                 400
```

Asn Thr Gly Asp Arg Gly Gln Thr Asn Asn Ala Ala Ser Ala Ser Ala
            405                 410                 415
Ser Asn Ser Thr
            420

<210> SEQ ID NO 2
<211> LENGTH: 394
<212> TYPE: PRT
<213> ORGANISM: Homo sapiens

<400> SEQUENCE: 2

Met Glu Tyr Met Pro Met Glu Gly Gly Met Ser Gly Arg Pro Arg
 1               5                  10                  15
Thr Thr Ser Phe Ala Glu Ser Cys Lys Pro Val Gln Gln Pro Ser Ala
                20                  25                  30
Phe Gly Ser Met Lys Val Ser Arg Asp Lys Asp Gly Ser Lys Val Thr
                35                  40                  45
Thr Val Val Ala Thr Pro Gly Gln Gly Pro Asp Arg Pro Gln Glu Val
 50                  55                  60
Ser Tyr Thr Asp Thr Lys Val Ile Gly Asn Gly Ser Phe Gly Val Val
 65                  70                  75                  80
Tyr Gln Ala Lys Leu Cys Asp Ser Gly Glu Leu Val Ala Ile Lys Lys
                85                  90                  95
Val Leu Gln Asp Lys Arg Phe Lys Asn Arg Glu Leu Gln Ile Met Arg
                100                 105                 110
Lys Leu Asp His Cys Asn Ile Val Arg Leu Arg Tyr Phe Phe Tyr Ser
                115                 120                 125
Ser Gly Glu Lys Lys Asp Glu Val Tyr Leu Asn Leu Val Leu Asp Tyr
                130                 135                 140
Val Pro Glu Thr Val Tyr Arg Val Ala Arg His Tyr Ser Arg Ala Lys
145                 150                 155                 160
Gln Thr Leu Pro Val Ile Tyr Val Lys Leu Tyr Met Tyr Gln Leu Phe
                165                 170                 175
Arg Ser Leu Ala Tyr Ile His Ser Phe Gly Ile Cys His Arg Asp Ile
                180                 185                 190
Lys Pro Gln Asn Leu Leu Leu Asp Pro Asp Thr Ala Val Leu Lys Leu
                195                 200                 205
Cys Asp Phe Gly Ser Ala Lys Gln Leu Val Arg Gly Glu Pro Asn Val
                210                 215                 220
Ser Tyr Ile Cys Ser Arg Tyr Tyr Arg Ala Pro Glu Leu Ile Phe Gly
225                 230                 235                 240
Ala Thr Asp Tyr Thr Ser Ser Ile Asp Val Trp Ser Ala Gly Cys Val
                245                 250                 255
Leu Ala Glu Leu Leu Leu Gly Gln Pro Ile Phe Pro Gly Asp Ser Gly
                260                 265                 270
Val Asp Gln Leu Val Glu Ile Ile Lys Val Leu Gly Thr Pro Thr Arg
                275                 280                 285
Glu Gln Ile Arg Glu Met Asn Pro Asn Tyr Thr Glu Phe Lys Phe Pro
                290                 295                 300
Gln Ile Lys Ala His Pro Trp Thr Lys Val Phe Arg Pro Arg Thr Pro
305                 310                 315                 320
Pro Glu Ala Ile Ala Leu Cys Ser Arg Leu Leu Glu Tyr Thr Pro Thr
                325                 330                 335
Ala Arg Leu Thr Pro Leu Glu Ala Cys Ala His Ser Phe Phe Asp Glu

```
                    340                 345                 350
Leu Arg Asp Pro Asn Val Lys His Pro Asn Gly Arg Asp Thr Pro Ala
            355                 360                 365

Leu Phe Asn Phe Thr Thr Gln Glu Leu Ser Ser Asn Pro Pro Leu Ala
        370                 375                 380

Thr Ile Leu Ile Pro Pro His Ala Arg Ile
385                 390

<210> SEQ ID NO 3
<211> LENGTH: 361
<212> TYPE: PRT
<213> ORGANISM: Homo sapiens

<400> SEQUENCE: 3

Met Glu Tyr Met Pro Met Glu Gly Gly Gly Ser Lys Val Thr Thr
1               5                   10                  15

Val Val Ala Thr Pro Gly Gln Gly Pro Asp Arg Pro Gln Glu Val Ser
            20                  25                  30

Tyr Thr Asp Thr Lys Val Ile Gly Asn Gly Ser Phe Gly Val Val Tyr
        35                  40                  45

Gln Ala Lys Leu Cys Asp Ser Gly Glu Leu Val Ala Ile Lys Lys Val
    50                  55                  60

Leu Gln Asp Lys Arg Phe Lys Asn Arg Glu Leu Gln Ile Met Arg Lys
65                  70                  75                  80

Leu Asp His Cys Asn Ile Val Arg Leu Arg Tyr Phe Phe Tyr Ser Ser
                85                  90                  95

Gly Glu Lys Lys Asp Glu Val Tyr Leu Asn Leu Val Leu Asp Tyr Val
            100                 105                 110

Pro Glu Thr Val Tyr Arg Val Ala Arg His Tyr Ser Arg Ala Lys Gln
        115                 120                 125

Thr Leu Pro Val Ile Tyr Val Lys Leu Tyr Met Tyr Gln Leu Phe Arg
    130                 135                 140

Ser Leu Ala Tyr Ile His Ser Phe Gly Ile Cys His Arg Asp Ile Lys
145                 150                 155                 160

Pro Gln Asn Leu Leu Leu Asp Pro Asp Thr Ala Val Leu Lys Leu Cys
                165                 170                 175

Asp Phe Gly Ser Ala Lys Gln Leu Val Arg Gly Glu Pro Asn Val Ser
            180                 185                 190

Tyr Ile Cys Ser Arg Tyr Tyr Arg Ala Pro Glu Leu Ile Phe Gly Ala
        195                 200                 205

Thr Asp Tyr Thr Ser Ser Ile Asp Val Trp Ser Ala Gly Cys Val Leu
    210                 215                 220

Ala Glu Leu Leu Leu Gly Gln Pro Ile Phe Pro Gly Asp Ser Gly Val
225                 230                 235                 240

Asp Gln Leu Val Glu Ile Ile Lys Val Leu Gly Thr Pro Thr Arg Glu
                245                 250                 255

Gln Ile Arg Glu Met Asn Pro Asn Tyr Thr Glu Phe Lys Phe Pro Gln
            260                 265                 270

Ile Lys Ala His Pro Trp Thr Lys Val Phe Arg Pro Arg Thr Pro Pro
        275                 280                 285

Glu Ala Ile Ala Leu Cys Ser Arg Leu Leu Glu Tyr Thr Pro Thr Ala
    290                 295                 300

Arg Leu Thr Pro Leu Glu Ala Cys Ala His Ser Phe Phe Asp Glu Leu
305                 310                 315                 320
```

```
Arg Asp Pro Asn Val Lys His Pro Asn Gly Arg Asp Thr Pro Ala Leu
            325                 330                 335

Phe Asn Phe Thr Thr Gln Glu Leu Ser Ser Asn Pro Pro Leu Ala Thr
            340                 345                 350

Ile Leu Ile Pro Pro His Ala Arg Ile
            355                 360

<210> SEQ ID NO 4
<211> LENGTH: 483
<212> TYPE: PRT
<213> ORGANISM: Homo sapiens

<400> SEQUENCE: 4

Met Ser Gly Gly Pro Ser Gly Gly Pro Gly Gly Ser Gly Arg
 1               5                  10                  15

Ala Arg Thr Ser Ser Phe Ala Glu Pro Gly Gly Gly Gly Gly Gly
            20                  25                  30

Gly Gly Gly Pro Gly Gly Ser Ala Ser Gly Pro Gly Gly Thr Gly Gly
            35                  40                  45

Gly Lys Ala Ser Val Gly Ala Met Gly Gly Gly Val Gly Ala Ser Ser
50                  55                  60

Ser Gly Gly Pro Gly Gly Ser Gly Gly Gly Ser Gly Gly Pro
65                  70                  75                  80

Gly Ala Gly Thr Ser Phe Pro Pro Gly Val Lys Leu Gly Arg Asp
                85                  90                  95

Ser Gly Lys Val Thr Thr Val Val Ala Thr Leu Gly Gln Gly Pro Glu
                100                 105                 110

Arg Ser Gln Glu Val Ala Tyr Thr Asp Ile Lys Val Ile Gly Asn Gly
                115                 120                 125

Ser Phe Gly Val Val Tyr Gln Ala Arg Leu Ala Glu Thr Arg Glu Leu
130                 135                 140

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
                165                 170                 175

Tyr Phe Phe Tyr Ser Ser Gly Glu Lys Lys Asp Glu Leu Tyr Leu Asn
                180                 185                 190

Leu Val Leu Glu Tyr Val Pro Glu Thr Val Tyr Arg Val Ala Arg His
                195                 200                 205

Phe Thr Lys Ala Lys Leu Thr Ile Pro Ile Leu Tyr Val Lys Val Tyr
210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
                260                 265                 270

Gly Glu Pro Asn Val Ser Tyr Ile Cys Ser Arg Tyr Tyr Arg Ala Pro
                275                 280                 285

Glu Leu Ile Phe Gly Ala Thr Asp Tyr Thr Ser Ser Ile Asp Val Trp
                290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
                325                 330                 335
```

```
Gly Thr Pro Thr Arg Glu Gln Ile Arg Glu Met Asn Pro Asn Tyr Thr
            340                 345                 350

Glu Phe Lys Phe Pro Gln Ile Lys Ala His Pro Trp Thr Lys Val Phe
            355                 360                 365

Lys Ser Arg Thr Pro Pro Glu Ala Ile Ala Leu Cys Ser Ser Leu Leu
            370                 375                 380

Glu Tyr Thr Pro Ser Ser Arg Leu Ser Pro Leu Glu Ala Cys Ala His
385                 390                 395                 400

Ser Phe Phe Asp Glu Leu Arg Cys Leu Gly Thr Gln Leu Pro Asn Asn
            405                 410                 415

Arg Pro Leu Pro Pro Leu Phe Asn Phe Ser Ala Gly Glu Leu Ser Ile
            420                 425                 430

Gln Pro Ser Leu Asn Ala Ile Leu Ile Pro Pro His Leu Arg Ser Pro
            435                 440                 445

Ala Gly Thr Thr Thr Leu Thr Pro Ser Ser Gln Ala Leu Thr Glu Thr
            450                 455                 460

Pro Thr Ser Ser Asp Trp Gln Ser Thr Asp Ala Thr Pro Thr Leu Thr
465                 470                 475                 480

Asn Ser Ser

<210> SEQ ID NO 5
<211> LENGTH: 447
<212> TYPE: PRT
<213> ORGANISM: Homo sapiens

<400> SEQUENCE: 5

Met Ser Gly Gly Gly Pro Ser Gly Gly Gly Pro Gly Gly Ser Gly Arg
  1               5                  10                  15

Ala Arg Thr Ser Ser Phe Ala Glu Pro Gly Gly Gly Gly Gly Gly Gly
             20                  25                  30

Gly Gly Gly Pro Gly Gly Ser Ala Ser Gly Pro Gly Gly Thr Gly Gly
             35                  40                  45

Gly Lys Ala Ser Val Gly Ala Met Gly Gly Gly Val Gly Ala Ser Ser
         50                  55                  60

Ser Gly Gly Pro Gly Gly Ser Gly Gly Gly Ser Gly Gly Pro
 65                  70                  75                  80

Gly Ala Gly Thr Ser Phe Pro Pro Gly Val Lys Leu Gly Arg Asp
             85                  90                  95

Ser Gly Lys Val Thr Thr Val Val Ala Thr Leu Gly Gln Gly Pro Glu
            100                 105                 110

Arg Ser Gln Glu Val Ala Tyr Thr Asp Ile Lys Val Ile Gly Asn Gly
            115                 120                 125

Ser Phe Gly Val Val Tyr Gln Ala Arg Leu Ala Glu Thr Arg Glu Leu
        130                 135                 140

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
            165                 170                 175

Tyr Phe Phe Tyr Ser Ser Gly Glu Lys Lys Asp Glu Leu Tyr Leu Asn
            180                 185                 190

Leu Val Leu Glu Tyr Val Pro Glu Thr Val Tyr Arg Val Ala Arg His
            195                 200                 205

Phe Thr Lys Ala Lys Leu Thr Ile Pro Ile Leu Tyr Val Lys Val Tyr
        210                 215                 220
```

```
Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
                260                 265                 270

Gly Glu Pro Asn Val Ser Tyr Ile Cys Ser Arg Tyr Tyr Arg Ala Pro
                275                 280                 285

Glu Leu Ile Phe Gly Ala Thr Asp Tyr Thr Ser Ser Ile Asp Val Trp
            290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
                325                 330                 335

Gly Thr Pro Thr Arg Glu Gln Ile Arg Glu Met Asn Pro Asn Tyr Thr
                340                 345                 350

Glu Phe Lys Phe Pro Gln Ile Lys Ala His Pro Trp Thr Lys Val Phe
                355                 360                 365

Lys Ser Arg Thr Pro Pro Glu Ala Ile Ala Leu Cys Ser Ser Leu Leu
                370                 375                 380

Glu Tyr Thr Pro Ser Ser Arg Leu Ser Pro Leu Glu Ala Cys Ala His
385                 390                 395                 400

Ser Phe Phe Asp Glu Leu Arg Cys Leu Gly Thr Gln Leu Pro Asn Asn
                405                 410                 415

Arg Pro Leu Pro Pro Leu Phe Asn Phe Ser Ala Gly Glu Leu Ser Ile
                420                 425                 430

Gln Pro Ser Leu Asn Ala Ile Leu Ile Pro Pro His Leu Arg Ser
                435                 440                 445

<210> SEQ ID NO 6
<211> LENGTH: 387
<212> TYPE: PRT
<213> ORGANISM: Homo sapiens

<400> SEQUENCE: 6

Ser Gly Lys Val Thr Thr Val Val Ala Thr Leu Gly Gln Gly Pro Glu
1               5                   10                  15

Arg Ser Gln Glu Val Ala Tyr Thr Asp Ile Lys Val Ile Gly Asn Gly
                20                  25                  30

Ser Phe Gly Val Val Tyr Gln Ala Arg Leu Ala Glu Thr Arg Glu Leu
            35                  40                  45

Val Ala Ile Lys Lys Val Leu Gln Asp Lys Arg Phe Lys Asn Arg Glu
        50                  55                  60

Leu Gln Ile Met Arg Lys Leu Asp His Cys Asn Ile Val Arg Leu Arg
65                  70                  75                  80

Tyr Phe Phe Tyr Ser Ser Gly Glu Lys Lys Asp Glu Leu Tyr Leu Asn
                85                  90                  95

Leu Val Leu Glu Tyr Val Pro Glu Thr Val Tyr Arg Val Ala Arg His
                100                 105                 110

Phe Thr Lys Ala Lys Leu Thr Ile Pro Ile Leu Tyr Val Lys Val Tyr
            115                 120                 125

Met Tyr Gln Leu Phe Arg Ser Leu Ala Tyr Ile His Ser Gln Gly Val
        130                 135                 140

Cys His Arg Asp Ile Lys Pro Gln Asn Leu Leu Val Asp Pro Asp Thr
```

-continued

```
            145                 150                 155                 160
Ala Val Leu Lys Leu Cys Asp Phe Gly Ser Ala Lys Gln Leu Val Arg
                    165                 170                 175

Gly Glu Pro Asn Val Ser Tyr Ile Cys Ser Arg Tyr Arg Ala Pro
                180                 185                 190

Glu Leu Ile Phe Gly Ala Thr Asp Tyr Thr Ser Ser Ile Asp Val Trp
                195                 200                 205

Ser Ala Gly Cys Val Leu Ala Glu Leu Leu Gly Gln Pro Ile Phe
            210                 215                 220

Pro Gly Asp Ser Gly Val Asp Gln Leu Val Glu Ile Ile Lys Val Leu
225                 230                 235                 240

Gly Thr Pro Thr Arg Glu Gln Ile Arg Glu Met Asn Pro Asn Tyr Thr
                245                 250                 255

Glu Phe Lys Phe Pro Gln Ile Lys Ala His Pro Trp Thr Lys Val Phe
                260                 265                 270

Lys Ser Arg Thr Pro Pro Glu Ala Ile Ala Leu Cys Ser Ser Leu Leu
                275                 280                 285

Glu Tyr Thr Pro Ser Ser Arg Leu Ser Pro Leu Glu Ala Cys Ala His
                290                 295                 300

Ser Phe Phe Asp Glu Leu Arg Cys Leu Gly Thr Gln Leu Pro Asn Asn
305                 310                 315                 320

Arg Pro Leu Pro Pro Leu Phe Asn Phe Ser Ala Gly Glu Leu Ser Ile
                325                 330                 335

Gln Pro Ser Leu Asn Ala Ile Leu Ile Pro Pro His Leu Arg Ser Pro
                340                 345                 350

Ala Gly Thr Thr Thr Leu Thr Pro Ser Ser Gln Ala Leu Thr Glu Thr
                355                 360                 365

Pro Thr Ser Ser Asp Trp Gln Ser Thr Asp Ala Thr Pro Thr Leu Thr
                370                 375                 380

Asn Ser Ser
385

<210> SEQ ID NO 7
<211> LENGTH: 351
<212> TYPE: PRT
<213> ORGANISM: Homo sapiens

<400> SEQUENCE: 7

Ser Gly Lys Val Thr Thr Val Val Ala Thr Leu Gly Gln Gly Pro Glu
1               5                   10                  15

Arg Ser Gln Glu Val Ala Tyr Thr Asp Ile Lys Val Ile Gly Asn Gly
                20                  25                  30

Ser Phe Gly Val Val Tyr Gln Ala Arg Leu Ala Glu Thr Arg Glu Leu
            35                  40                  45

Val Ala Ile Lys Lys Val Leu Gln Asp Lys Arg Phe Lys Asn Arg Glu
            50                  55                  60

Leu Gln Ile Met Arg Lys Leu Asp His Cys Asn Ile Val Arg Leu Arg
65                  70                  75                  80

Tyr Phe Phe Tyr Ser Ser Gly Glu Lys Lys Asp Glu Leu Tyr Leu Asn
                85                  90                  95

Leu Val Leu Glu Tyr Val Pro Glu Thr Val Tyr Arg Val Ala Arg His
                100                 105                 110

Phe Thr Lys Ala Lys Leu Thr Ile Pro Ile Leu Tyr Val Lys Val Tyr
                115                 120                 125
```

```
Met Tyr Gln Leu Phe Arg Ser Leu Ala Tyr Ile His Ser Gln Gly Val
    130                 135                 140

Cys His Arg Asp Ile Lys Pro Gln Asn Leu Leu Val Asp Pro Asp Thr
145                 150                 155                 160

Ala Val Leu Lys Leu Cys Asp Phe Gly Ser Ala Lys Gln Leu Val Arg
                165                 170                 175

Gly Glu Pro Asn Val Ser Tyr Ile Cys Ser Arg Tyr Tyr Arg Ala Pro
            180                 185                 190

Glu Leu Ile Phe Gly Ala Thr Asp Tyr Thr Ser Ser Ile Asp Val Trp
        195                 200                 205

Ser Ala Gly Cys Val Leu Ala Glu Leu Leu Leu Gly Gln Pro Ile Phe
    210                 215                 220

Pro Gly Asp Ser Gly Val Asp Gln Leu Val Glu Ile Lys Val Leu
225                 230                 235                 240

Gly Thr Pro Thr Arg Glu Gln Ile Arg Glu Met Asn Pro Asn Tyr Thr
                245                 250                 255

Glu Phe Lys Phe Pro Gln Ile Lys Ala His Pro Trp Thr Lys Val Phe
                260                 265                 270

Lys Ser Arg Thr Pro Pro Glu Ala Ile Ala Leu Cys Ser Ser Leu Leu
            275                 280                 285

Glu Tyr Thr Pro Ser Ser Arg Leu Ser Pro Leu Glu Ala Cys Ala His
        290                 295                 300

Ser Phe Phe Asp Glu Leu Arg Cys Leu Gly Thr Gln Leu Pro Asn Asn
305                 310                 315                 320

Arg Pro Leu Pro Pro Leu Phe Asn Phe Ser Ala Gly Glu Leu Ser Ile
                325                 330                 335

Gln Pro Ser Leu Asn Ala Ile Leu Ile Pro Pro His Leu Arg Ser
            340                 345                 350

<210> SEQ ID NO 8
<211> LENGTH: 15
<212> TYPE: PRT
<213> ORGANISM: Artificial Sequence
<220> FEATURE:
<223> OTHER INFORMATION: N-terminus addition sequence

<400> SEQUENCE: 8

Glu Phe Met Pro Thr Glu Ala Met Ala Ala Pro Lys Arg Val Ile
1               5                   10                  15

<210> SEQ ID NO 9
<211> LENGTH: 9
<212> TYPE: PRT
<213> ORGANISM: Artificial Sequence
<220> FEATURE:
<223> OTHER INFORMATION: N-terminus addition sequence

<400> SEQUENCE: 9

Glu Tyr Met Pro Met Glu Gly Gly Gly
1               5

<210> SEQ ID NO 10
<211> LENGTH: 6
<212> TYPE: PRT
<213> ORGANISM: Artificial Sequence
<220> FEATURE:
<223> OTHER INFORMATION: elution peptide

<400> SEQUENCE: 10

Glu Tyr Met Pro Thr Asp
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: Peptide substrate phosphorylatable by GSK3
<220> FEATURE:
<221> NAME/KEY: VARIANT
<222> LOCATION: 2, 3, 4
<223> OTHER INFORMATION: Xaa = Any Amino Acid

<400> SEQUENCE: 11

Ser Xaa Xaa Xaa Ser
 1               5
```